United States Patent [19]
Mishani et al.

[11] Patent Number: 6,126,917
[45] Date of Patent: Oct. 3, 2000

[54] EPIDERMAL GROWTH FACTOR RECEPTOR BINDING COMPOUNDS FOR POSITRON EMISSION TOMOGRAPHY

[75] Inventors: Eyal Mishani, Mevaseret Zion; Thomas Bonasera, Jerusalem; Giuseppina Ortu, Jerusalem; Yulia Rozen, Jerusalem; Aviv Gazit, Jerusalem; Alexander Levitzki, Burla, all of Israel

[73] Assignee: Hadasit Medical Research Services and Development Ltd., Jerusalem, Israel

[21] Appl. No.: 09/322,979

[22] Filed: Jun. 1, 1999

[51] Int. Cl.[7] .................. C07D 239/94; A61K 51/04
[52] U.S. Cl. .................. 424/1.89; 544/293; 382/131
[58] Field of Search .................. 544/293; 128/922; 382/131; 536/564; 424/1.89

[56] References Cited

U.S. PATENT DOCUMENTS 5,710,158 1/1998 Myers et al. .................. 514/256

FOREIGN PATENT DOCUMENTS 566 226 1/1993 European Pat. Off. .

OTHER PUBLICATIONS

Lowry and Richardson, Mechanism and Theory in Organic Chemistry, 3rd Edition, Harper and Row, New York, 1987, p. 633.

Roberts and Caserio, "Basic Principles of Organic Chemistry", Wa A. Benjamin, New York, 1964, p. 800–802.

Bridges et al, "Tyrosine Kinase Inhibitors. 8. An Unusually Steep Structure–Activity Relationship for Analogues of 4–(3–Bromoanilino)–6,7–dimethoxyquinazoline (PD 153035, a Potent Inhibitor of the Epidermal Growth Factor Receptor", *J. Med. Chem.*, 39: 267–276, 1996.

Johnstrom et al, "Synthesis of [methoxy–$^{11}$C]PD153035, a Selective EGF Receptor Tyrosine Kinase Inhibitor", *J. Labelled Compounds and Radiopharmaceuticals*, 41(7): 623–629, 1998 (abstract).

Mulholland et al, "Synthesis and Biodistribution of New C–11 and F–18 Labeled Epidermal Growth Factor Receptor Ligands", *J. Nucl. Med.*, 36 (Suppl): 71P.

*Primary Examiner*—Mark Berch
*Assistant Examiner*—Thomas McKenzie
*Attorney, Agent, or Firm*—Mark M. Friedman

[57] ABSTRACT

A radiolabeled compound of a formula:

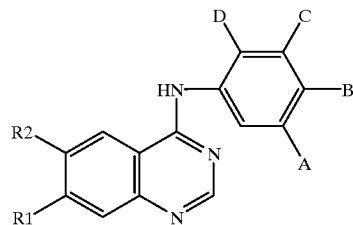

is described. R1 and R2 are each independently selected from the group consisting of hydrogen, alkyl, hydroxy, alkoxy, halo, haloalkyl, carboxy, carbalkoxy and salts thereof; and A, B, C and D are each independently selected from the group consisting of a hydrogen and an electron withdrawing group, provided that at least one of A, B, C and D is [18]fluorine.

9 Claims, 1 Drawing Sheet

EPIDERMAL GROWTH FACTOR RECEPTOR BINDING COMPOUNDS FOR POSITRON EMISSION TOMOGRAPHY

FIELD AND BACKGROUND OF THE INVENTION

The present invention relates to novel fluorinated Positron Emission Tomography (PET) biomarkers, and, more particularly, to a fluorinated biomarkers for quantification of epidermal growth factor receptor tyrosine kinase.

Positron Emission Tomography (PET), a nuclear medicine imagine technology which allows the three-dimensional, quantitative determination of the distribution of radioactivity within the human body, is becoming an increasingly important tool for the measurement of physiological, biochemical, and pharmacological function at a molecular level, both in healthy and pathological states. PET requires the administration to the subject of a molecule labeled with a positron-emitting nuclide (radiotracer) such as $^{15}O$, $^{13}N$, $^{11}C$, and $^{18}F$, which have half-lives of 2, 10, 20, and 110 minutes, respectively.

Polypeptides such as growth factors, differentiation factors, and hormones often mediate their pleiotropic actions by binding to and activating cell surface receptors with an intrinsic intracellular protein tyrosine kinase activity. Epidermal growth factor receptor-tyrosine kinase (EGFR-TK) is over expressed in breast cancer and other neoplasia. A suitable radiotracer that binds to EGFR-TK might allow, through a nuclear medicine imaging technique such as PET, the mapping and quantification of this receptor-kinase. This would allow the study of changes in levels of expression of this receptor, including the monitoring of response to hormonal or other chemotherapy, and could lead to better patient management and differentiation in regard to therapeutic course of action.

Recently, $^{99m}Tc$-labeled anti EGFR antibody was synthesized and biodistribution and dosimetry studies were performed in humans [1, 2]. However this labeled antibody, similar to other protein radiopharmaceuticals, has high and prolonged retention of radioactivity in the liver which constitutes a major problem for clinical applications. Furthermore, these researchers found that it was difficult to obtain accurate quantification of activity in tumors within normal organs because of varying background activities, particularly in lung lesions where fluid and atelectasis could not be differentiated from tumor.

EGF itself has been labeled for nuclear medicine imaging with gamma emitting nuclides including $^{99m}Tc$ [3, 4] and $^{111}In$ [5, 6], and the positron-emitting nuclide $^{76}Br$ [7, 8]. The biodistribution in normal rats of the latter, [$^{76}Br$]EGF (murine), was reported [8], but no other in vivo studies in laboratory animals or humans have been reported.

4-Anilinoquinazolines have been shown to potently and selectively inhibit EGFR-TK activity by binding reversibly to an inner membrane ATP binding site on EGFR-TK, the prototype for such compounds being the small-molecules PD 153035 [9] and AG1478 [10] (see Table 1 below). A report of a radioiodinated analog of PD 153035 including in vitro binding studies in MDA-486 cells has been presented [11]. PD 153035 labeled with $^{11}C$ in the 6,7-methoxy groups has been evaluated in rats implanted with human neuroblastoma xenografts (SH-SY5Y) but specific uptake was not determined in a blocking study [12]. PD 153035 was also labeled with $^{11}C$ specifically in the 7-methoxy position and biodistribution experiments were performed in normal mice, but uptake specificity could not be demonstrated as administration of an enzyme-blocking dose of PD 153035 caused an increase in tracer uptake in the tissues studied [13]. The same abstract reported the labeling of the 7-(2-fluoroethoxy) PD 153035 analog with $^{18}F$, but no biological experiments with this tracer were described. Additionally, the 2-[$^{18}F$] fluoroethyl group might be subject to a high rate of [$^{18}F$] hydrogen fluoride elimination to give the corresponding alkene ether, potentially resulting in high uptake of $^{18}F$ in bone, giving poor in vivo images. Further, these ultra potent ($IC_{50}$<30 pM) inhibitors may only measure flow or permeability surface area rather than biochemical changes [14]. And, PD 153035 has been shown to undergo metabolism to four compounds, two of which have been identified as the 6- and 7-monodemethylated derivatives, compounds which maintain potency for EGFR-TK inhibition [15]. Thus labeling in the 6- or 7-alkoxy groups as described above, would lead to radioactive metabolites that do not bind EGFR-TK.

Another approach to small molecules as EGFR-TK PET tracers are 4-anilinoquinazoline derivatives labeled with $^{18}F$ on the aniline ring (see reference [16]). Assuming that metabolism of PD 153035 arylfluoro derivatives is similar to the metabolism of PD 153035 itself, in this approach the monodemethylated derivatives would retain the radiolabel and should maintain affinity for EGFR-TK. While the presence in the blood of three compounds with potential to bind the target would complicate kinetic compartmental modeling, the probability of accumulation of radioactivity in the target would be increased. $^{18}F$'s half life, five times longer than the half life of $^{11}C$, affords a wider time-window for PET measurements than $^{11}C$ does, possibly allowing the benefit of imaging after disappearance of blood radioactivity and washout of radiotracer nonspecific binding. Since PD 153035 plasma levels decrease from a maximum to 2% of the maximum after approximately 3 hours [15], later imaging, perhaps an hour or more postinjection (virtually impossible with $^{11}C$), may give a more pure signal of EGFR-TK presence. In addition, labeling the aniline ring may result in a more inherently metabolically stable tracer that will lead to low nonspecific uptake of radioactivity in, e.g., bone. Additional related art is disclosed in U.S. Pat. No. 5,710,158; EP 566226B1 and CA 2,086,968.

There is thus a widely recognized need for, and it would be highly advantageous to have, novel fluorinated PET biomarkers devoid of the above limitations.

SUMMARY OF THE INVENTION

According to one aspect of the present invention there is provided a compound of a formulae:

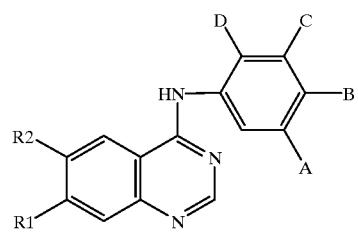

wherein:

R1 and R2 are each independently selected from the group consisting of hydrogen, alkyl, hydroxy, alkoxy, halo, haloalkyl, carboxy, carbalkoxy and salts thereof; and A, B, C and D are each independently selected from the group consisting of a hydrogen and an electron withdrawing group, provided that at least one of A, B, C and D is an electron withdrawing group.

According to still further features in the described preferred embodiments A and B are each a chlorine atom, C is a hydrogen atom and D is a fluorine atom.

According to still further features in the described preferred embodiments A is fluor atom, B and D are each a hydrogen atom, and C is a $CF_3$ group.

According to still further features in the described preferred embodiments A is a fluorine atom and B, C and D are each a hydrogen atom.

According to still further features in the described preferred embodiments B is a fluorine atom and A, C and D are each a hydrogen atom.

According to another aspect of the present invention there is provided a method of inhibiting tyrosine kinase activity of epidermal growth factor receptor comprising the step of subjecting the epidermal growth factor receptor to the compound described above and which is further described and its activity exemplified in the following sections.

According to yet another aspect of the present invention there is provided a method of treating a patient having impaired tyrosine kinase activity of epidermal growth factor receptor comprising the step of administering to the patient the compound described above and which is further described and its activity exemplified in the following sections.

According to still another aspect of the present invention there is provided a radiolabeled compound of a formulae:

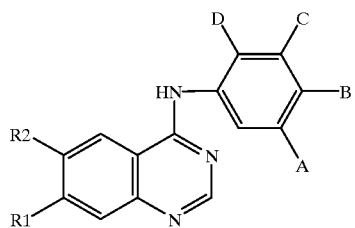

wherein:

R1 and R2 are each independently selected from the group consisting of hydrogen, alkyl, hydroxy, alkoxy, halo, haloalkyl, carboxy, carbalkoxy and salts thereof; and A, B, C and D are each independently selected from the group consisting of a hydrogen and an electron withdrawing group, provided that at least one of A, B, C and D is [$^{18}$]fluorine.

According to further features in preferred embodiments of the invention described below, A and B are each a chlorine atom, C is a hydrogen atom and D is the [$^{18}$]fluorine.

According to still further features in the described preferred embodiments A is the [$^{18}$]fluorine, B and D are each a hydrogen atom, and C is a $CF_3$ group.

According to still further features in the described preferred embodiments A is the [$^{18}$]fluorine and B, C and D are each a hydrogen atom.

According to still further features in the described preferred embodiments B is the [$^{18}$]fluorine and A, C and D are each a hydrogen atom.

According to further features in preferred embodiments of the invention described below, the electron withdrawing group is selected from the group consisting of a halogen, $SO_3H$, $NO_2$, CN and $CF_3$.

According to still farther features in the described preferred embodiments the halogen is selected from the group consisting of iodine, chlorine, bromine and fluorine.

According to yet an additional aspect of the present invention there is provided a method of monitoring the level of epidermal growth factor receptor within a body of a patient comprising the steps of (a) administering to the patient the radiolabeled compound described above; and employing a nuclear imaging technique for monitoring a distribution of the compound within the body or within a portion thereof.

According to still further features in the described preferred embodiments the technique is positron emission tomography.

According to still further features in the described preferred embodiments the compounds described herein has $IC_{50}$ values for inhibition of tyrosine kinase activity of epidermal growth factor receptor of between 0.1 and 120 nM.

According to an additional aspect of the present invention there is provided a pharmaceutical composition comprising as an active ingredient any of the compounds described herein and a pharmaceutically acceptable carrier.

According to a further aspect of the present invention there is provided a method of synthesizing a compound of a general formulae:

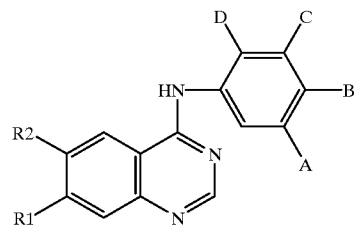

wherein R1 and R2 are each independently selected from the group consisting of hydrogen, alkyl, hydroxy, alkoxy, halo, haloalkyl, carboxy, carbalkoxy and salts thereof; and A, B, C and D are each independently selected from the group consisting of a hydrogen and an electron withdrawing group, provided that at least one of A, B, C and D is an electron withdrawing group; the method comprising the step of coupling a 6-R1, 7-R2 derivatized 4-chloroquinazoline with an aniline derivatized by the A, B, C and D.

According to still a further aspect of the present invention there is provided a method of synthesizing a radiolabeled compound of a general formulae:

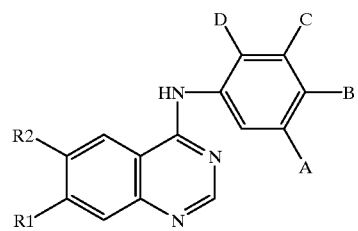

wherein R1 and R2 are each independently selected from the group consisting of hydrogen, alkyl, hydroxy, alkoxy, halo, haloalkyl, carboxy, carbalkoxy and salts thereof; and A, B, C and D are each independently selected from the group consisting of a hydrogen and an electron withdrawing group, provided that at least one of A, B, C and D is a [$^{18}$]fluorine; the method comprising the step of coupling a 6-R1, 7-R2 derivatized 4-chloroquinazoline with an aniline derivatized by the A, B, C and D.

The present invention successfully addresses the shortcomings of the presently known configurations by providing new biomarkers for PET.

BRIEF DESCRIPTION OF THE DRAWINGS

The invention is herein described, by way of example only, with reference to the accompanying drawings, wherein.

DESCRIPTION OF THE PREFERRED EMBODIMENTS

Figure 1:
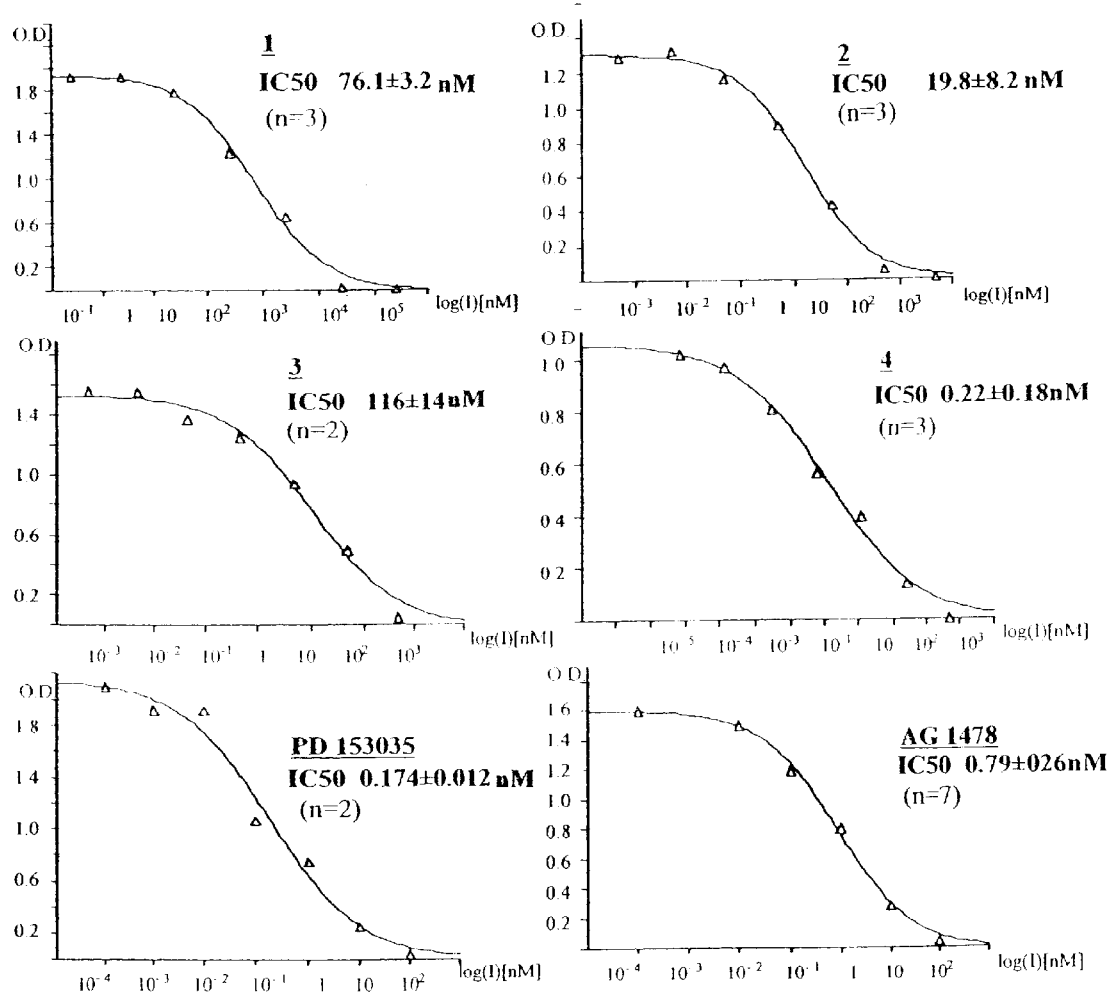
FIG. 1 demonstrates autophosphorylation inhibition curves for the four fluorinated compounds according to the present invention (compounds 1–4) and two reference compounds.

The present invention is of novel compounds which can be used as epidermal growth factor receptor tyrosine kinase inhibitors. Specifically, in their radiolabeled form, the novel compounds can be used as biomarkers for quantification of epidermal growth factor receptor tyrosine kinase using Positron Emission Tomography (PET).

The principles and operation of the present invention may be better understood with reference to the drawings and accompanying descriptions.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

According to one aspect of the present invention there is provided a compound of a formulae:

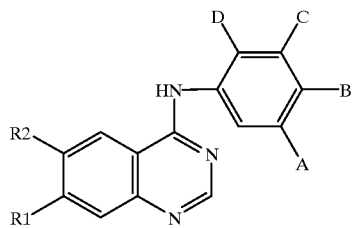

wherein:

R1 and R2 are each independently selected from the group consisting of hydrogen, alkyl, hydroxy, alkoxy, halo, haloalkyl, carboxy, carbalkoxy and salts thereof; and A, B, C and D are each independently selected from the group consisting of a hydrogen and an electron withdrawing group, provided that at least one of A, B, C and D is an electron withdrawing group.

Several compounds corresponding to the above formulae where synthesized (see Table 1 below) and their $IC_{50}$ values with respect to epidermal growth factor receptor tyrosine kinase activity ranged between 0.1 and 120 nM. The present invention is therefore directed specifically at compounds having $IC_{50}$ values with respect to epidermal growth factor receptor tyrosine kinase activity in the range of 0.1–120 nM, preferably 0.1–60 nM, more preferably 0.1–30 nM, more preferably 0.1–15 nM, more preferably 0.1–10 nM, more preferably 0.1–5 nM, more preferably 0.1–1 nM, most preferably 0.1–0.5 nM, most preferably, below 0.3 nM.

In one compound thus prepared and which is referred to hereinbelow as compound 4, A and B are each a chlorine atom, C is a hydrogen atom and D is a fluorine atom. The $IC_{50}$ of compound 4 toward epidermal growth factor receptor tyrosine kinase activity was measured to be 0.22±0.18 nM.

In another compound thus prepared and which is referred to hereinbelow as compound 3, A is fluor atom, B and D are each a hydrogen atom, and C is a $CF_3$ group. The $IC_{50}$ of compound 3 toward epidermal growth factor receptor tyrosine kinase activity was measured to be 116±14 nM.

In yet another compound thus prepared and which is referred to hereinbelow as compound 2, A is a fluorine atom and B, C and D are each a hydrogen atom. The $IC_{50}$ of compound 2 toward epidermal growth factor receptor tyrosine kinase activity was measured to be 19.8±8.2 nM.

In still another compound thus prepared and which is referred to hereinbelow as compound 1, B is a fluorine atom and A, C and D are each a hydrogen atom. The $IC_{50}$ of compound 1 toward epidermal growth factor receptor tyrosine kinase activity was measured to be 76.1±3.2 nM.

The R1 and R2 in compounds 1–4 are methoxy groups. It will however be appreciated by one ordinarily skilled in the art that compounds having other groups such as hydrogen, alkyl, hydroxy, alkoxy, halo, haloalkyl, carboxy, carbalkoxy and salts thereof can be readily prepared following the protocols described below, while changing the starting materials accordingly.

R1 and R2 selection influence the hydrophylicity of the compounds and affects their distribution is fat. Compounds which are less likely to be adsorbed in fat are presently preferred. Compounds having a pair of hydroxyls are less hydrophobic and are therefore expected to be less adsorbed in fat.

The compounds described herein can be used to inhibit epidermal growth factor receptor tyrosine kinase activity which typically results in autophosphorylation and activation in cases of impaired activity thereof. As such, these compounds can be used to treat cancers or other neoplasia characterized by elevation in epidermal growth factor receptor tyrosine kinase activity, due, for example, to overexpression.

As used herein the term "treat" or its equivalent term "treating" includes substantially inhibiting, slowing or reversing the progression of a disease, substantially ameliorating clinical symptoms of a disease or substantially preventing the appearance of clinical symptoms of a disease.

According to another aspect of the present invention there is provided a radiolabeled compound of a formulae:

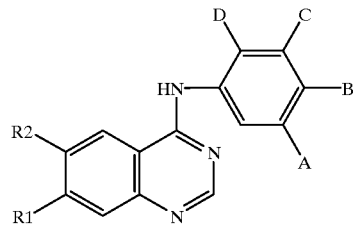

wherein:

R1 and R2 are each independently selected from the group consisting of hydrogen, alkyl, hydroxy, alkoxy, halo, haloalkyl, carboxy, carbalkoxy and salts thereof;

A, B, C and D are each independently selected from the group consisting of a hydrogen and an electron withdrawing group, provided that at least one of A, B, C and D is [$^{18}$]fluorine.

Several compounds corresponding to the above formulae where synthesized (see Table 1 below).

In one compound thus prepared and which is referred to hereinbelow as [$^{18}$F]compound 4, A and B are each a chlorine atom, C is a hydrogen atom and D is the [$^{18}$F] fluorine.

In another compound thus prepared and which is referred to hereinbelow as [3'$^{18}$F]compound 3, A is the [$^{18}$F]fluorine, B and D are each a hydrogen atom, and C is a $CF_3$ group.

In yet another compound thus prepared and which is referred to hereinbelow as [$^{18}$F]compound 2, A is the [$^{18}$F] fluorine and B, C and D are each a hydrogen atom.

In still another compound thus prepared and which is referred to hereinbelow as [$^{18}$F]compound 1, B is the [$^{18}$F]fluorine and A, C and D are each a hydrogen atom.

For each of the compounds herein described the electron withdrawing group can be a halogen (iodine, chlorine, bromine and fluorine), $SO_3H$, $NO_2$, CN and $CF_3$. The number, type and position of the electron withdrawing group(s) affect the affinity, as determined, for example, by $IC_{50}$, of the compound to the receptor.

The radiolabeled compounds herein described can be used to effect a method of monitoring the level of epidermal growth factor receptor within a body of a patient by administering to the patient any of the radiolabeled compound described herein; and employing a nuclear imaging technique, e.g., positron emission tomography, for monitoring a distribution of the compound within the body or within a portion thereof.

Any of the compounds described herein, both the non-labeled and the radiolabeled compounds, can be formulated into a pharmaceutical composition which can be used for treatment of a disease or for nuclear imaging. Such a composition includes as an active ingredient any of the compounds, both radiolabeled or non-labeled, described herein and a pharmaceutically acceptable carrier.

Thus, for therapeutic or prophylactic treatment of diseases, disorders or medical conditions, or for nuclear imaging the compounds of the present invention can be formulated in a pharmaceutical composition, which may include thickeners, carriers, buffers, diluents, surface active agents, preservatives, and the like, all as well known in the art. Pharmaceutical compositions may also include one or more active ingredients, such as, but not limited to, anti inflammatory agents, anti microbial agents, anesthetics and the like in addition to the compounds described herein.

The pharmaceutical composition may be administered in either one or more of ways depending on whether local or systemic treatment or administration is of choice, and on the area to be treated or diagnosed. Administration may be done topically (including ophtalmically, vaginally, rectally, intranasally), orally, by inhalation, or parenterally, for example by intravenous drip or intraperitoneal, subcutaneous, intramuscular or intravenous injection.

Formulations for topical administration may include but are not limited to lotions, ointments, gels, creams, suppositories, drops, liquids, sprays and powders. Conventional pharmaceutical carriers, aqueous, powder or oily bases, thickeners and the like may be necessary or desirable.

Compositions for oral administration include powders or granules, suspensions or solutions in water or non-aqueous media, sachets, capsules or tablets. Thickeners, diluents, flavorings, dispersing aids, emulsifiers or binders may be desirable.

Formulations for parenteral administration may include, but are not limited to, sterile solutions which may also contain buffers, diluents and other suitable additives. Slow release compositions are envisaged for treatment.

Nuclear imaging dosing depend on the affinity of the compound to its receptor, the isotope employed and the specific activity of labeling. Persons ordinarily skilled in the art can easily determine optimum nuclear imaging dosages and dosing methodology.

Treatment dosing is dependent on severity and responsiveness of the condition to be treated, but will normally be one or more doses per day, with course of treatment lasting from several days to several months or until a cure is effected or a diminution of disease state is achieved. Persons ordinarily skilled in the art can easily determine optimum dosages, dosing methodologies and repetition rates.

Additional objects, advantages, and novel feature s of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion.

Materials and Experimental Methods

4-Amino-6,7-dimethoxyquinazoline (AG 1477) [18] and 3-fluoro-5-trifluoromethylaniline [17] were prepared according to published methods. All other chemicals were purchased from Sigma Chemical Co. (St. Louis, Mo.), Fisher Scientific (Pittsburgh, Pa.), Aldrich Co. (Milwaukee, Wis.) or Carlo Erba. Chemicals were used as supplied, except DMSO which was stored over activated molecular sieves for at least one day prior to use. Microwave heating was performed in a conventional oven (BR 740XL, Brother) operating at 500 W (full power). Mass spectroscopy was performed in EI mode on an LKB 2091 gas chromatograph-mass spectrometer at the Hadassah-Hebrew University mass spectroscopy facility. $^1$H-NMR spectra were obtained on a Bruker AMX 400 MHz, using tetramethylsilane as internal standard. Elemental analysis was performed at the Hebrew University microanalysis laboratory.

[$^{18}$F]Fluoride ion was produced by the $^{18}$O(p, n)$^{18}$F nuclear reaction on ~350 $\mu$l enriched [$^{18}$O]water (97% isotopic purity, Rotem, Israel) as a target in the Hadassah-Hebrew University IBA 18/9 cyclotron (Belgium). Reactive organic [$^{18}$F]fluoride ion was prepared by adding 10–50 $\mu$L irradiated target water to Kryptofix®2.2.2 (10 mg, 27 $\mu$l) and $K_2CO_3$ (1 mg) in water-acetonitrile. Azeotropic removal of water with acetonitrile was achieved by heating under a stream of nitrogen. The dried Kryptofix® 2.2.2—potassium [$^{18}$F]fluoride was then dissolved in 300 $\mu$L anhydrous DMSO for use in radiolabeling.

HPLC was performed on a Varian 9012Q pump, a Varian 9050 variable wavelength UV detector operating at 254 nm, and a Bioscan Flow-Count radioactivity detector with a NaI crystal. Labeled compounds were purified on a normal phase system using a silica column (5 $\mu$m, 250×10 mm, Primesphere, Phenomenex) and the following mobile phase system: hexane-dichloromethane-methanol, 50:48:2; at 10 minutes, gradient to 35:60:5 over 30 minutes; 5 mL/minutes. Eluent fractions (2.5 ml) were collected on a fraction collector (FC205, Gilson). Analysis of formulated radiotracers was performed on a reversed phase system using a C18 column (5 $\mu$m, 250×4.6 mm, Econosil, Alltech) and the following mobile phase system: water-methanol, 20:80; 1 ml/minutes.

Radiotracer formulation was performed as follows: Selected semi-preparative eluent fractions were transferred to a glass flask and the solution was concentrated in vacuo to dryness. The residue was dissolved in 0.5 ml EtOH and 0.5 ml isotonic saline. The solution was filtered through an EtOH-wetted Millex-FG filter (0.2 $\mu$m, Millipore), and another 4 ml saline was used to rinse the flask and filter, providing a 5 ml, 10% EtOH, 90% saline formulation.

Synthesis of 4-[(4-Fluorophenyl)amino]-6,7-dimethoxyquinazoline (compound 1):

4-Chloro-6,7-dimethoxyquinazoline (50 mg, 0.22 mmol) and 4-fluoroaniline (21 $\mu$L, 0.22 mmol) were placed in a dry two-neck flask and a condenser was adjusted. DMF (6 mL) was added and the mixture was heated to 130° C. for 30 minutes. After cooling the precipitate was filtered washed with EtOH and dried in a vacuum oven (50° C.). The product was obtained as the hydrochloride salt in 94% yield (70 mg). $^1$HNMR [((CD$_3$)$_2$SO) $\delta$9.47(s, 1H), 8.42(s, 1H), 7.8(s, 1H), 7.77(m,2H), 7.23(m, 2H), 7.17(s, 1H), 3.94(s, 3H), 3.91(s, 3H). MS, m/e: 300 (M$^+$), 299 [(M-H)$^+$]. Anal. Calcd. for C$_{16}$H$_{15}$FClN$_3$O$_2$: C, 57.14; H, 4.46; N, 12.50. Found: C, 57.16; H, 4.49; N, 12.38.

Synthesis of 4-[(3-Fluorophenyl)amino]-6,7-dimethoxyquinazoline (compound 2):

Employing the same method used for compound 1, 4-chloro-6,7-dimethoxyquinazoline (113 mg, 0.5 mmol) and 3-fluoroaniline (48 $\mu$L, 0.5 mmol) afforded compound 2 as the hydrochloride salt in 98% yield (166 mg). $^1$H NMR [((CD$_3$)$_2$SO) $\delta$11.59(s, 1H), 8.85(s, 1H), 8.43(s, 1H), 7.7(m, 1H), 7.6(m,1H), 7.5(m, 1H), 7.4(s, 1H), 7.1(s, 1H), 4.1(s, 3H), 3.96(s, 3H). MS, m/e: 300 (M$^+$), 299 [(M-H)$^+$]. Anal. Calcd. for C$_{16}$H$_{15}$FClN$_3$O$_2$: C, 57.14; H, 4.46; N, 12.50. Found: C, 57.09; H, 4.53; N, 12.49.

Synthesis of $^4$-[(3-Fluoro-5-trifluoromethylphenyl)amino]-6,7-dimethoxyquinazoline (compund 3):

4-Chloro-6,7-dimethoxyquinazoline (113.5 mg, 0.5 mmol) and 3-fluoro-5-trifluoromethylaniline [17] (93 mg, 0.52 mmol) were placed in a dry two-neck flask and a condenser was adjusted. EtOH (8 mL) was added and the mixture was refluxed for 60 minutes. After cooling the precipitate was filtered washed with EtOH and dried in a vacuum oven (50° C.). The product was obtained as the hydrochloride salt in 78% Yield (159.5 mg). $^1$H NMR [((CD$_3$)$_2$SO) $\delta$8.71(s, 1H), 8.09(m, 1H), 7.64(s, 1H), 7.3(bs, 1H), 7.1(m,1H), 7.0(m, 1H), 4.05(s, 3H), 3.90(s, 3H). MS,/e: 368 (M$^+$). Anal. Calcd. for C$_{17}$H$_{14}$F$_4$ClN$_3$O$_2$: C, 50.49; H, 3.46; N, 10.39. Found: C, 50.47; H, 3.59; N, 10.34.

Synthesis of 3,4-Dichloro-6-fluoroaniline (compound 8):

3,4-Dichloro-6-fluoronitrobenzene (compound 9, 474 mg) in 9:1 EtOH-water (7 mL) was added dropwise to a refluxing mixture of 500 $\mu$L hydrazine hydrate, 60 mg Raney® Nickel in 7 mL Ethanol-water 9:1. After the addition was completed, reflux was maintained for additional 25 minutes. After cooling to room temperature, the mixture was filtered and the solvent evaporated. Purification by silica flesh column chromatography gave 192.5 mg of pure compound 8. $^1$H NMR [(CDCl$_3$) $\delta$7.1(d, J=11 Hz, 1H), 6.8(d, J=11 Hz, 1H). MS, m/e: 179 ([M-H]$^+$).

Synthesis of 4-[(3,4-Dichloro-6-fluorophenyl)amino]-6,7-dimethoxyquinazoline (compound 4):

4-Chloro-6,7-dimethoxyquinazoline (128.3 mg, 0.56 mmol) and 3,4-dichloro-6-fluoroaniline (compound 8, 88.5 mg, 0.49 mmol) were placed in a dry two-neck flask and a condenser was adjusted. iPrOH (6 mL) was added and the mixture heated to 85° C. and treated with 5 $\mu$L of HCl (conc.). Reflux was maintained for 30 minutes. After cooling the precipitate was filtered washed with EtOH and dried in a vacuum oven (50° C.). The product was obtained as the hydrochloride salt in 84% Yield (167.5 mg). $^1$H NMR [(CDCl$_3$) $\delta$8.91(d, J=8 Hz, 1H), 8.7(s, 1H), 7.29(d, J=10 Hz, 1H), 7.28(s, 1H), 6.9(s, 1H), 4.04(s,3H), 4.02(s, 3H). MS,m/e: 369 (M$^+$). Anal. Calcd. for C$_{16}$H$_{13}$FCl$_3$N$_3$O$_2$: C,47.4; H, 3.21; N, 10.4. Found: C, 47.65; H,3.21; N, 10.08.

Autophosphorylation Inhibition Experiments:

EGFR-TK source: As a source of EGFR-TK, A431 human epidermoid carcinoma cell lysate was used. A431 cells were grown in DMEM containing 10% fetal calf serum and antibiotics penicillin and streptomycin). After several days, the cells were removed from the flasks by incubation at 37° C. with PBS/i mM EDTA buffer for 1 hour. The pellet obtained with centrifugation of the cell suspension (600 g×5 minutes at room temperature) was then resuspended in lysis buffer (0.02 M Hepes pH 7.4, 0.125 M NaCl, 1% Triton X-100, 10% glycerol) and left in ice for 10 minutes. Cell lysate was obtained with a further centrifugation (10,000 rpm×10 minutes at 4° C.), and the supernatant was collected and frozen at −70° C. in aliquots.

ELISA assay: EGFR-TK autophosphorylation IC50 values were obtained by means an ELISA assay. All the following incubations were performed at room temperature and with constant shaking. After each step the plate was washed with water (5×) and TBST buffer (1×). The final volume for each well was 150 $\mu$l. A Corning 96 well ELISA plate was coated with monoclonal anti EGFR antibody m108 (Sugen Inc.) diluted in PBS (pH 8.2), and kept overnight at 4° C.

After removing the unbound m108, the plate was washed and PBS containing 5% milk (1% fat) was added for the blocking (25 minutes). One aliquot of A431 cell lysate was thawed and added to the plate. The amount of lysate was defined according to a previous test performed without inhibitors for the definition of the best ratio between the amount of m108 and the amount of EGFR-TK in the A431 cell lysate.

After 25 minutes, seven different concentrations of each inhibitor were added, and for each case one well was left as a control. All inhibitors were diluted in TBS/DMSO and the final concentration of DMSO was 0.05% in each well (including the controls).

After 25 minutes, and without washing the plate, ATP/MnCl$_2$ solution was added in each well. The final concentration was 3 $\mu$M ATP/5 mM MnCl$_2$. In this step the temperature was kept at 26° C. and the plate was under constant shaking. The incubation with ATP/MnCl$_2$ was for 5 minutes.

Then, to stop the phosphorylation reaction, EDTA was added (pH 8, final concentration in each well 20 mM) and after 1 minute all the plate was washed.

Afterward, polyclonal anti-phosphotyrosine serum (Sugen, Inc.) was added (dilution of antibody in TBST containing 5% milk). The incubation was for 45 minutes.

For the calorimetric detection of phosphotyrosine in EGFR-TK, TAGO anti-rabbit peroxidase conjugate antibody (Sugen, Inc.) was added in TBST/5% milk solution (45 minutes).

After washing, the colorimetric reaction was performed by adding ABTS/H$_2$O$_2$ in citrate-phosphate buffer. After 5–10 minutes the plate was read on Dynaytec MR 5000 ELISA reader at 405 nm.

The analysis of the data was performed with "Regression" software.

Since the exact concentrations of m108 in the stock solution and EGFR-TK in the cell lysate were unknown, an experiment was performed to determine the optimal dilution of m108 stock and lysate. Stock m108 (approx. 0.2–0.5 μg/μl) was diluted 1:400, 1:600, 1:800 and 1:1000 with PBS, while A431 cell lysate was diluted 1:2, 1:4, 1:6, 1:8, and 1:10. At the end of the experiment, the chosen dilutions of m108 and A431 cell lysate were those in which optical densities were around 1.2–1.4 and 0.09–0.1 for the control group (performed with the same dilutions of m108 and lysate but without adding ATP for the phosphorylation reaction).

Synthesis of 4-[(4-[$^{18}$F]Fluorophenyl)amino]-6,7-dimethoxyquinazoline ([$^{18}$F] compound 1):

The Kryptofix®2.2.2—potassium [$^{18}$F]fluoride—DMSO solution described above was added to 2–3 mg 1,4-dinitrobenzene in a screw-top test tube (8 mL, Corning). The tube was capped, shaken and heated in a microwave for 3.5 minutes. After cooling in an ambient water bath, the vial contents were diluted with 10 mL water and loaded onto an activated (EtOH) and equilibrated (water) C18 Sep-Pak (classic, short body, Waters). The cartridge was washed with water (10 mL) and the desired intermediate, 4-[$^{18}$F]fluoro-1-nitrobenzene, was eluted with EtOH (2 mL) into a small glass test tube. The reduction vessel was prepared by adding to a flat-bottomed glass vial (25 mL), sequentially, a few borosilicate glass beads, 100 μl 4:1 EtOH-water, 250 μL Raney® Nickel slurry, and 60 μL hydrazine monohydrate. After capping with a septum-equipped screw cap (vented with a large diameter needle) the vial was shaken and placed in a 40° C. heating block. The ethanolic 4-[$^{18}$F]fluoro-1-nitrobenzene solution was diluted with 0.5 mL water and added slowly to the reduction vessel. After 5 minutes, the vessel was cooled in an ambient water bath, and the vial content was filtered through a 0.45 μm filter (Puradisc, polypropylene, Whatman) into another flat-bottomed 25 mL vial. To the filtered solution were added 8 mL water and 10 mL ether and by capping and inverting several times to mix, the reduction product, 4-[$^{18}$F]fluoroaniline, was extracted into the ether layer. An 8 mL screw-top test tube was charged with 4–5 mg AG 1477 and 300 μL 2-propanol. The ethereal radioaniline solution was added to the tube by passing it through MgSO$_4$ (2 g) and a new 0.45 μm filter. The ether was removed under He, while warming the tube in an ambient water bath. Concentrated HCl (1 μl) was added and the capped tube was heated in a 110° C. oil bath for 15 minutes. After cooling the tube in ambient water, the acid was neutralized and the free base liberated with the addition of 50 μL 5 M NaOH. Dichloromethane (0.3 mL) and hexane (0.3 mL) were added to the tube and the solution was filtered through a 0.2 μm filter (Acrodisc, nylon. Gelman) and injected onto the semi-preparative normal phase HPLC system described. [$^{18}$F]compound 1 eluted with a $t_R$ of 33.7 minutes and was formulated as described with a yield of 11% from potassium [$^{18}$F]fluoride. The formulation was then analyzed by reversed phase HPLC ($t_R$=8.76 minutes; chemical purity=89%; radiochemical purity>95%). At formulation, [$^{18}$F]compund 1 had a specific radioactivity of 363 Ci/mmol (13 GBq/μmol).

Synthesis of 4-[(3-[$^{18}$F]Fluoro-5-trifluoromethylphenyl)amino]-6,7-dimethoxyquinazoline ([3'-$^{18}$F]compound 3):

The general procedure was similar to that used to synthesize [$^{18}$F]compound 1 described above, with the following exceptions: In place of 1,4-dinitrobenzene, 2–3 mg 3,5-dinitrobenzotrifluoride was used in the reaction with [$^{18}$F]fluoride ion to provide 3-[$^{18}$F]fluoro-5-nitrobenzotrifluoride; in place of a liquid-liquid extraction following the reduction step, a second C18 Sep-Pak extraction was used, and elution of 3-[$^{18}$F]fluoro-5-trifluoromethylaniline was achieved with 2 ml ether. Normal phase semi-preparative HPLC ($t_R$=36.4 minutes) provided ([3'-$^{18}$F]compound 3). Formulated ([3'-$^{18}$F]compund 3) (7% overall yield) was analyzed by reversed phase HPLC ($t_R$=11.6 minutes) indicating>95% radiochemical purity, >95% chemical purity and 460 Ci/mmol (17 GBq/μmol) specific radioactivity at formulation.

Synthesis of 4-[(3,4-Dichloro-6-[$^{18}$F]fluorophenyl)amino]-6,7-dimethoxyquinazoline ([$^{18}$F]compound 4):

The general procedure was similar to that used to synthesize [$^{18}$F]compund 3 described above, with the following exceptions: In place of 3,5-dinitrobenzotrifluoride, 2–3 mg 1,2-dichloro-4,5-dinitrobenzene was used in the reaction with [$^{18}$F]fluoride ion to provide 1,-dichloro-4-[$^{18}$F]fluoro-5-nitrobenzene. Normal phase semi-preparative HPLC ($t_R$=31.7 minutes) provided ([$^{18}$F]compund 4). Formulated ([$^{18}$F]compound 4) (4% overall yield) was analyzed by reversed phase HPLC ($t_R$=9.1 minutes) indicating>95 % radiochemical purity, ~90% chemical purity and 430 Ci/mmol (16 GBq/μmol) specific radioactivity.

Experimental Results

In a search for $^{18}$F-labeled EGFR-TK PET tracers, four compounds, 1–4, were prepared as candidates for future $^{18}$F-labeling (Table 1).

TABLE 1

Structures and inhibition concentrations

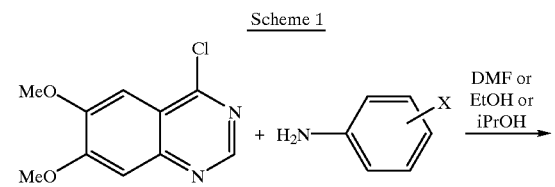

Substitution (ring position) Autophosphorylation

| Compound | A (3') | B (4') | C (5') | D (6') | nM* | IC$_{50}$ |
|---|---|---|---|---|---|---|
| 1 | H | F | H | H | 76.1 ± 3.2(3) | |
| 2 | F | H | H | H | 19.8 ± 8.2(2) | |
| 3 | F | H | CF$_3$ | H | 116 ± 14(2) | |
| 4 | Cl | Cl | H | F | 0.22 ± 0.18(3) | |
| PD 153035 | Br | H | H | H | 0.174 ± 0.012(2) | |
| AG 1478 | Cl | H | H | H | 0.79 ± 0.26(7) | |

*All values shown were determined using an identical method presented as average ± SEM with the number of replicate analyses indicated in parentheses.

All four compounds were prepared by coupling 4-chloro-6,7-ethoxyquinazoline with the corresponding aniline derivative in DMF, H or acidic iPrOH (Scheme 1).

Scheme 1

-continued

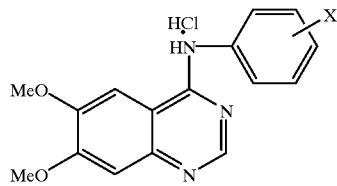

After 30–60 minutes reflux, the final products were obtained as the hydrochloride salts in approximately 80–90% yield. In the case of compound 3 3-fluoro-5-trifluoromethyl-nitrobenzene (compund 5) was initially prepared by reacting the dinitro derivative (compound 6) with potassium fluoride and Kryptofix®2.2.2 as phase transfer catalyst in DMSO solution (Scheme 2) [17].

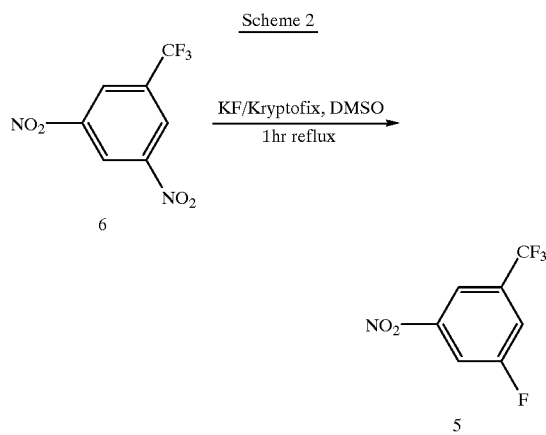

Synthon (compound 5) was then reduced in ethanolic solution of hydrazine hydrate and Raney® nickel to furnish the 3-fluoro-5-trifluoromethyl-aniline (compound 7) in 70% overall yield (Scheme 3) [17].

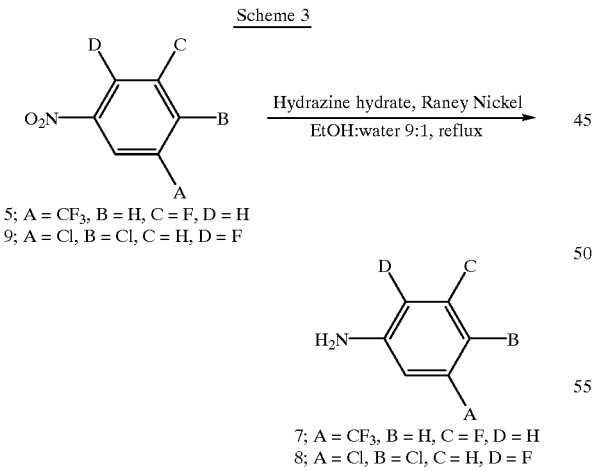

Compound 4 was chosen based on the high inhibition activity of 3'-chlorine-containing AG 1478 and because of the symmetrical nature of the starting material to be used in the radiosynthesis, 1,2-dichloro-4,5-dinitrobenzene, which would facilitate the incorporation of $^{18}F$. The aniline derivative (compound 8) was obtained from the corresponding nitrobenzene (compound 9) after reduction under the same conditions as described above (Scheme3).

EGFR-TK autophosphorylation $IC_{50}$ values were measured for the four fluorinated compounds in order to determine their potential as PET tracers. The method employed an ELISA assay based on an anti-EGFR antibody. Plots of example inhibition curves are shown in FIG. 1 and the results are summarized in Table 1 above. For compound 1, substitution of a fluorine atom at the para position on the aniline ring resulted in a moderate (relative to PD 153035 or AG 1478) $IC_{50}$ of 76 nM. When the fluorine atom was placed at the meta position the biological activity increased and $IC_{50}$ of 19.8 nM was measured for compound 2. However, this value is higher by two orders of magnitude than the values for AG 1478 and PD 153035 where a heavier halogen such as chlorine or bromine is bonded to the meta position of the aniline ring. It is known that substitution of trifluoromethyl group on aryl moiety in biologically active compounds in most cases enhances the biological activity. However, in this particular case the $IC_{50}$ measured for compound 3, which contains the trifluoromethyl group at the 5 position in addition to the fluorine atom at the meta position, was higher than that of compound 2 (116 nM). Based on the autophosphorylation $IC_{50}$ values, compound 4 was found to be the most potent inhibitor with an $IC_{50}$ of 0.22 nM, reflecting the importance of the chlorine atom at the meta position. The addition of a chlorine atom at the para position and fluorine at the 6 position contribute to the potency of compound 4 and resulted in an $IC_{50}$ value which is lower than the one obtained for AG 1478.

Each of compounds 1, 2, 3 and 4 was prepared according to Scheme 4, following the same synthetic strategy used to make the non-labeled compounds.

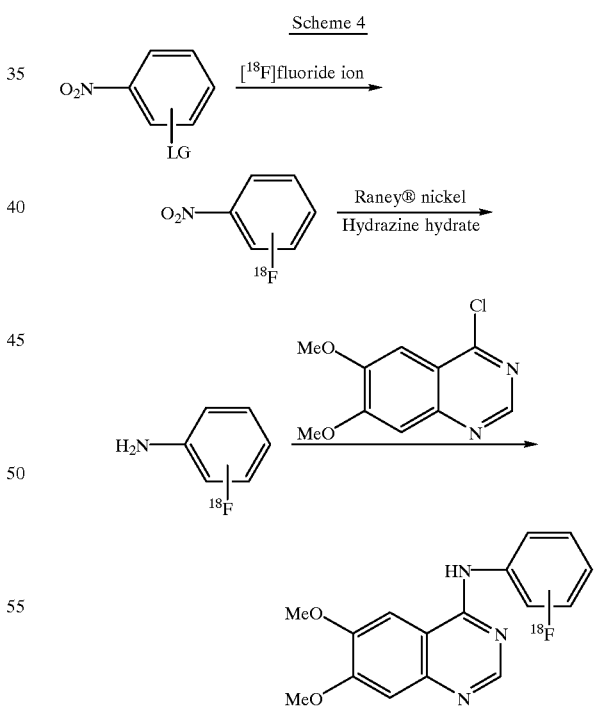

An aryl dinitro derivative was reacted with organic [$^{18}F$] fluoride ion in DMSO to give the corresponding aryl [$^{18}F$] fluoronitro derivative in estimated yields of 30% (compound 2) or 60–80% (compounds 1 and 3–4). A conventional microwave oven was used to heat the reaction mixture. Following C18 solid phase extraction, the nitro residue was reduced to an amino residue in Raney® nickel at 40° C. The moderate temperature and short reaction time (5 minutes) were critical, as higher temperatures and longer times resulted in apparent over reduction of the [$^{18}$F]fluoroaniline and loss of radioactivity on the Raney® nickel. The resulting [$^{18}$F]fluoroaniline was then isolated by filtration and either C18 solid phase or ether-water liquid-liquid extraction (yields for compounds 1 and 3–4 averaged about 75%, lower yields were obtained for compound 2). The final reaction mixture was prepared by adding the dried ethereal radioaniline solution to an iPrOH solution of 4-chloro-6,7-dimethoxyquinazoline. The ether was removed by evaporation in a stream of helium gas at room temperature. Performing the ether evaporation in the presence of iPrOH was critical, as evaporation of the ether-radioaniline solution alone either in vacuo (using a rotary evaporator) or under helium gas either with or without heating, resulted in significant or complete co-volatilization of the radioaniline. After acidifying the reaction mixture, the reaction proceeded to the final labeled tracers, [$^{18}$F]compound 1, [$^{18}$F]compound 2, [3'-$^{18}$F]compound 3 and [$^{18}$F]compund 4, in overall non-decay-corrected yields of about 1% for compound 2 and 4–12% for compounds 1 and 3–4 (from potassium [$^{18}$F]fluoride and based on the final, formulated product). The entire process was completed within ~120–150 minutes of radionuclide production. In all cases, the products were radiochemically pure. The chemical purity of each formulation, measured by HPLC at 254 nm, remained high at 89% to >95%. Specific radioactivity averages, measured at formulation, ranged 363–460 Ci/mmol (13–17 GBq/μmol).

Thus, a method was developed for the synthesis of fluorinated EFGR-TK ATP-site inhibitors. Three were found to be of moderate potency and one, compound 4, was a very potent EGFR-TK autophosphorylation inhibitor. The four compounds, including highly potent compound 4, were successfully radiolabeled with $^{18}$F in yields suitable for further use as biological tracers. These compounds can therefore be used to measure differences in EGFR-TK expression and ATP binding site fractional occupancy in vitro and in vivo and be used as PET tracers in, for example, cancer diagnosis, staging and therapy protocol selection, e.g., in predicting which patients would benefit from EGF-directed therapeutic approaches such as those based on anti-EGF antibodies, EGF-directed fusion toxins, or EGFR-TK inhibitors.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

REFERENCES

1. Escobar, N. I.; Morales, A. M.; Ducong?, J.; Torres, I. C.; Fernandez, E.; Gomez, J. A. Pharmacokinetics, biodistribution and dosimetry of 99mTc-labeled anti-human epidermal growth factor receptor humanized monoclonal antibody R3 in rats. *Nucl. Med. Biol.* 1998, 25, 17–23.

2. Iznaga-Escobar, N.; Torres, L. A.; Morales, A.; Ramos, M.; Alvarez, I.; Perez, N.; Fraxedas, R.; Rodr?guez, O.; Rodriguez, N.; Perez, R.; Lage, A.; Stabin, M. G. *J. Nucl. Med.* 1998, 39, 15–23.

3. Capala, J.; Barth, R. F.; Bailey, M. Q.; Fenstermaker, R. A.; Marek, M. J.; Rhodes, B. A. Radiolabeling of epidermal growth factor with Tc and in vivo localization following intracerebral injection into normal and glioma-bearing rats. *Bioconjug. Chem.* 1997, 8, 289–295.

4. Holmberg, A.; Marquez, M.; Westlin, J.-E.; Nilsson, S. Labeling of polypeptides with technetium-99 m using a dextran spacer. *Cancer Res.* 1995, 55, 5710s–5713s.

5. Remy, S.; Reilly, R. M.; Sheldon, K.; Gariepy, J. A new radioligand for the epidermal growth factor receptor: In labeled human epidermal growth factor derivatized with a bifinctional metal-chelating peptide. *Bioconjugate Chem.* 1995, 6, 683–690.

6. Reilly, R. M.; Gariepy, J. Investigation of factors influencing the sensitivity of tumor imaging with phantoms and a receptor binding radiopharmaceutical. *J. Nucl. Med.* 1996, 37 (supplement), 199P (abstract number 911).

7. Scott-Robson, S.; Capala, J.; Malmborg, P.; Lundqvist, H. Production of Br and its use in labeling proteins. *Acta Radiol. Suppl.* 1991, 376, 64.

8. Scott-Robson, S.; Capala, J.; Carlsson, J.; Malmborg, P.; Lundqvist, H. Distribution and stability in the rat of a Br/I-labeled polypeptide, epidermal growth factor. *Int. J. Appl. Instrum.[B]* 1991, 18, 241–246.

9. Fry, D. W.; Kraker, A. J.; McMichael, A.; Arnbroso, L. A.; Nelson, J. M.; Leopold, W. R.; Connors, R. W.; Bridges, A. J. A specific inhibitor of the epidermal growth factor receptor tyrosine kinase. *Science* 1994, 265, 1093–1095.

10. Levitzki, A.; Gazit, A. *Science* 1995 267, 1782–1788.

11. Mulholland, G. K.; Winkle, W.; Mock, B. H.; Sledge, G. *J. Nucl. Med.* 1995, 36 (supplement), 71P.

12. Johnstrom P., Fredriksson A., Thorell J.-O., and Stone-Elander S.—*J. Labelled Cpd. Radiopharm.* 41: 623 (1998).

13. Mulholland, G. K.; Zheng, Q.-H.; Winkle, W. L.; Carlson, K. A. *J. Nucl. Med.* 1997, 38, 141P (abstract number 529).

14. Eckelman, W. C. The application of receptor theory to receptor-binding and enzyme-binding oncologic radiopharmaceuticals. *Nucl. Med. Biol.* 1994, 21, 759–769.

15. Kunkel, M. W.; Hook, K. E.; Howard, C. T.; Przybranowski, S.; Roberts, B. J.; Elliot, W. L.; Leopold, W. R. Inhibition of the epidermal growth factor receptor tyrosine kinase by PD 153035 in human A431 tumors in athymic nude mice. *Invest. New Drugs* 1996, 13, 295–302.

16. Lim, J. K.; Riese, D. J.; Negash, K.; Hawkins, R. A.; VanBrocklin, H. F. Synthesis and in vitro evaluation of epidermal growth factor receptor tyrosine kinase inhibitors. *J. Nucl. Med.,* 1998, 39, 20P–21P (conference abstract)

17. Mishani E., Cristel M. E., Dence C. S., McCarthy T. J., and Welch M. J.—*Nuc. Med. Biol.* 24: 269 (1997).

18. Gazit A., Chen J., App G., McMahon G., Hirth P., Chen I., Levitzki A. Biorg. Med. Chem. 8:1203–1207 (1996).

What is claimed is:

1. A radiolabeled compound of a formulae:

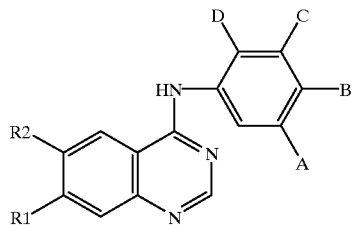

wherein:
R1 and R2 are each independently selected from the group consisting of hydrogen, alkyl, hydroxy, alkoxy, halo, haloalkyl, carboxy, carbalkoxy and salts thereof; and A, B, C and D are each independently selected from the group consisting of a hydrogen and an electron withdrawing group, provided that at least one of A, B, C and D is [$^{18}$]fluorine.

2. The compound of claim 1, wherein said electron withdrawing group is selected from the group consisting of a halogen, $SO_3H$, $NO_2$, CN and $CF_3$.

3. The compound of claim 1, wherein said halogen is selected from the group consisting of iodine, chlorine, bromine and fluorine.

4. The compound of claim 1, wherein A and B are each a chlorine atom, C is a hydrogen atom and D is said [$^{18}$]fluorine.

5. The compound of claim 1, wherein A is said [$^{18}$]fluorine, B and D are each a hydrogen atom, and C is a $CF_3$ group.

6. The compound of claim 1, wherein A is said [$^{18}$]fluorine and B, C and D are each a hydrogen atom.

7. The compound of claim 1, wherein B is said [$^{18}$]fluorine and A, C and D are each a hydrogen atom.

8. A method of monitoring the level of epidermal growth factor receptor within a body of a patient comprising the steps of:
(a) administering to the patient the compound of claim 1;
(b) employing a positron emission tomography for monitoring a distribution of the compound within the body or within a portion thereof.

9. A method of synthesizing a compound of a formula:

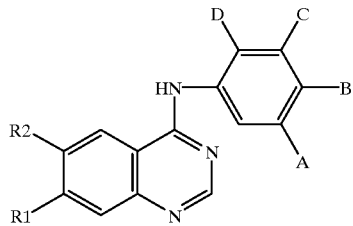

wherein R1 and R2 are each independently selected from the group consisting of hydrogen, alkyl, hydroxy, alkoxy, halo, haloalkyl, carboxy, carbalkoxy and salts thereof; and A, B, C and D are each independently selected from the group consisting of a hydrogen and an electron withdrawing group, provided that at least one of A, B, C and D is a [$^{18}$]fluorine; the method comprising the step of coupling a 6-R1, 7-R2 derivatized 4-chloroquinazoline with an aniline substituted by said A, B, C and D.

* * * * *

UNITED STATES PATENT AND TRADEMARK OFFICE
CERTIFICATE OF CORRECTION

PATENT NO.    : 6,126,917
DATED         : October 3, 2000
INVENTOR(S)   : Mishani et al.

It is certified that error appears in the above-identified patent and that said Letters Patent is hereby corrected as shown below:

<u>Title page,</u>
Item [75], inventors, after Alexander Levitski change "Burla" to -- Jerusalem --
Item [73], Assignee, add -- Yissum Research Services and Development Ltd., Jerusalem --

Signed and Sealed this

Second Day of July, 2002

*Attest:*

JAMES E. ROGAN
*Attesting Officer*    *Director of the United States Patent and Trademark Office*